US00PP37498P2

(12) United States Plant Patent
Renault

(10) Patent No.: US PP37,498 P2
(45) Date of Patent: Jun. 30, 2026

(54) ***HYDRANGEA* PLANT NAMED 'RENMETA'**

(50) Latin Name: *Hydrangea paniculata*
Varietal Denomination: RENMETA

(71) Applicants: Thierry Renault, Gorron (FR); Eric Renault, Gorron (FR); Anne Renault, Gorron (FR)

(72) Inventor: Jean Renault, Gorron (FR)

( * ) Notice: Subject to any disclaimer, the term of this patent is extended or adjusted under 35 U.S.C. 154(b) by 0 days.

(21) Appl. No.: 19/021,449

(22) Filed: Jan. 15, 2025

(51) Int. Cl.
*A01H 5/02* (2018.01)

(52) U.S. Cl.
USPC ..... Plt./250

(58) Field of Classification Search
USPC ..... Plt./250
See application file for complete search history.

(56) References Cited

PUBLICATIONS https://www.youtube.com/watch?v=MGL44NICRQc (Year: 2024).*
https://pitomnik-nastino.ru/market/gortenzii/gortenzii_metelchatye/gortenziya_metel_chataya_metallica_s2/ (Year: 2022).*
http://hortenzija.lv/index.php?route=product/product&product_id=229 (Year: 2024).*

* cited by examiner

*Primary Examiner* — Susan Mccormick Ewoldt
*Assistant Examiner* — Zachariah Allan Kay

(57) ABSTRACT

A new and distinct cultivar of *Hydrangea* plant named 'Renmeta' is disclosed, characterized by mophead panicles of sterile flowers which have sepals that open light green with a light pink edge then mature to entirely red-pink. Plants are short, semi-upright and have distinct red flower stems. Foliage is small and dark green. The new variety is a *Hydrangea*, typically produced as an ornamental plant.

3 Drawing Sheets

Latin name of the genus and species: *Hydrangea paniculata.*

Variety denomination: 'RENMETA'.

BACKGROUND OF THE INVENTION

The new cultivar is a product of a planned breeding program conducted by the inventor to produce new *Hydrangea paniculata* cultivars for ornamental purposes. The crossing resulting in the new cultivar was made at a commercial nursery in Gorron, France. The parental varieties are unknown.

The inventor has filed an application with the CPVO Nov. 23, 2020, having application number 2020/2773. This disclosure falls within the exception allowed under 102(b)(1).

SUMMARY OF THE INVENTION

The cultivar 'RENMETA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RENMETA'. These characteristics in combination distinguish 'RENMETA' as a new and distinct *Hydrangea* cultivar:

1. Mophead panicles.
2. Flower sepals which open light green with a light pink edge then mature to entirely red-pink.
3. Short plants.
4. Semi-upright plant habit.

5. Distinct red flower stems.
6. Small, dark green foliage.

PARENTAL COMPARISON

The parent varieties are unknown.

COMMERCIAL COMPARISON

Plants of 'RENMETA' can be compared to plants of the commercial cultivar *Hydrangea paniculata* 'Renxolor', unpatented. Plants of 'RENMETA' are similar to plants of 'Renxolor', in most horticultural characteristics, however, plants of 'RENMETA' differ in the following:

1. Flower panicles of the new cultivar are larger than flower panicles of this comparator'
2. Sterile flower color of the new cultivar is white, light green, light pink and finally dark red-pink; flower color of this comparator is white and light pink.

BRIEF DESCRIPTION OF THE PHOTOGRAPHS

The accompanying photograph in FIG. 1 illustrates in full color a close-up of typical inflorescences of 'RENMETA' during June of 2020 in Gorron, France. This plant is approximately 1-year old and field grown. The sterile flowers are fully open and show the typical initial white, pink and green coloration.

Figure 1:
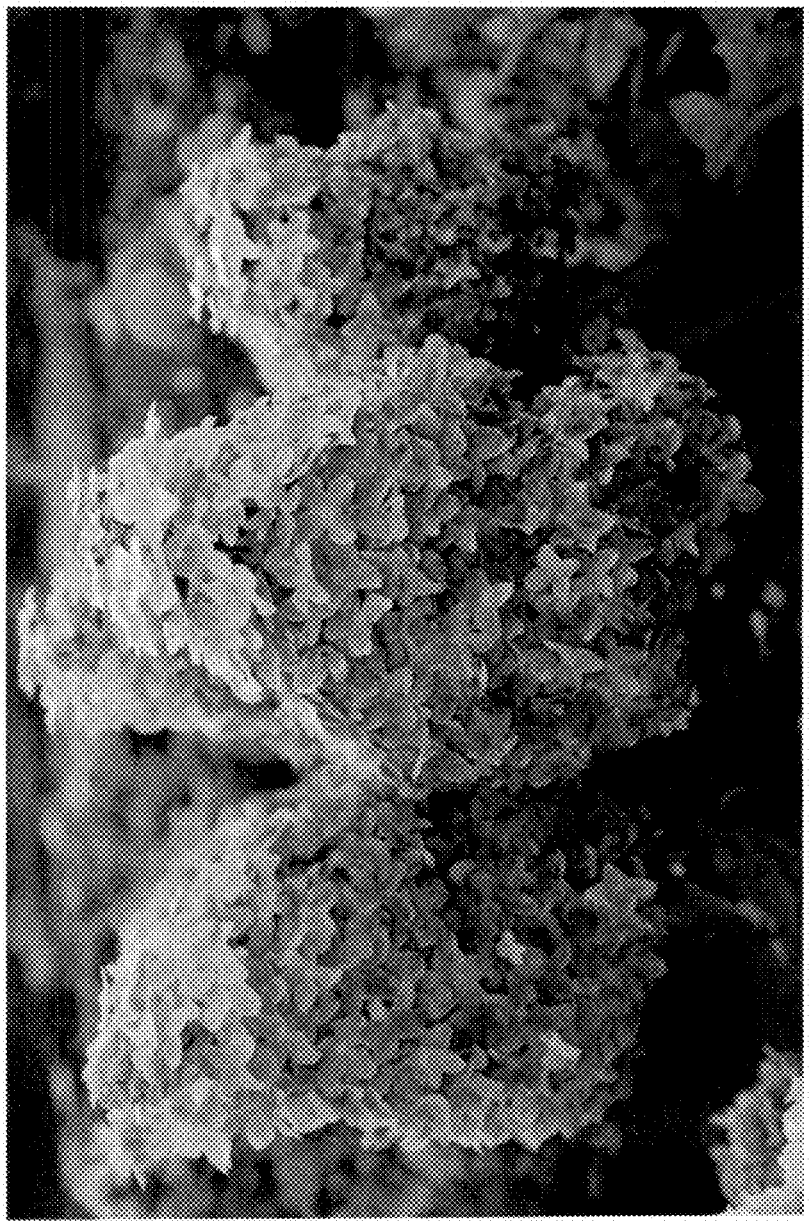
Figure 2:
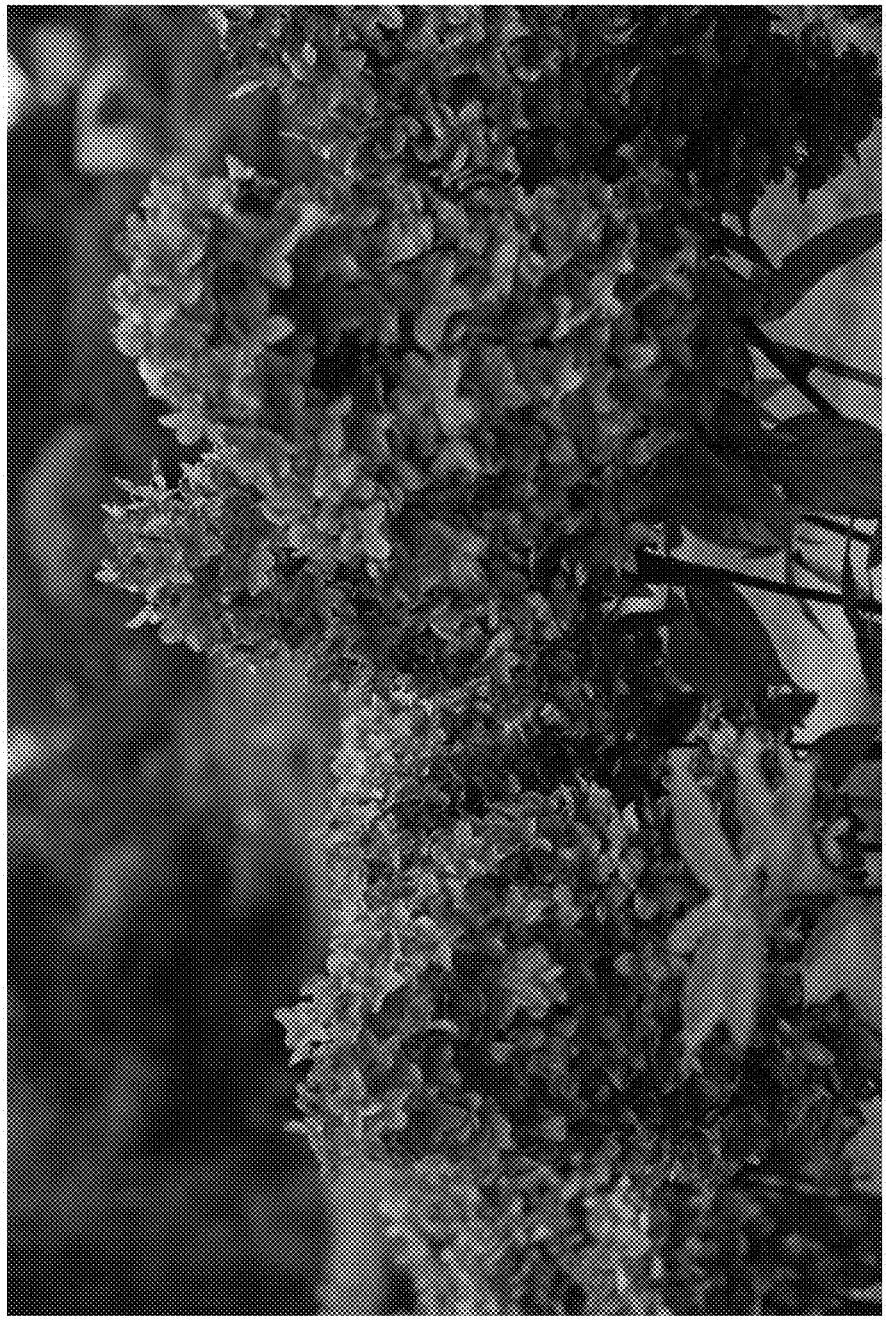
FIG. 2 illustrates in full color a color a close-up of a mature inflorescence of 'RENMETA' during September. The sterile flowers have turned red-pink.
Figure 3:
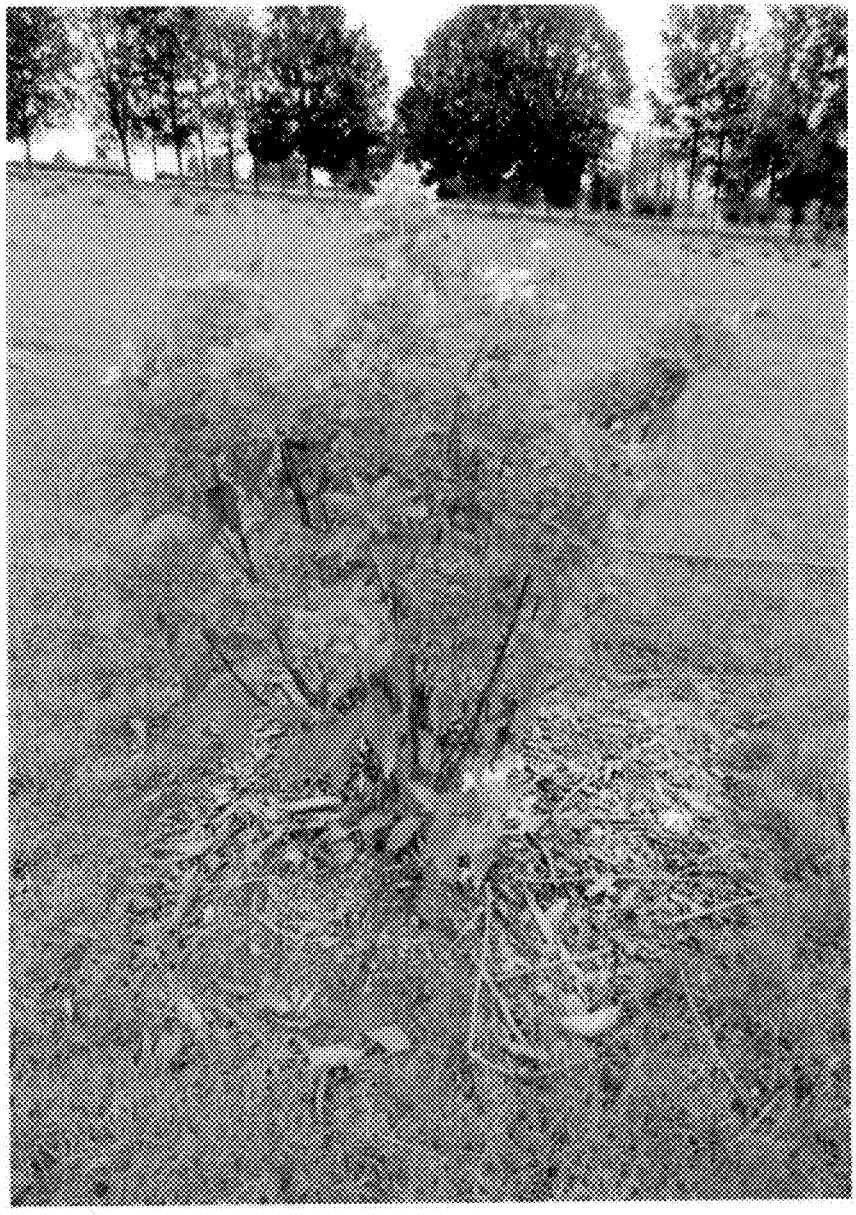
FIG. 3 illustrates in full color a field-grown plant of 'RENMETA' at about 3-year old during August.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'RENMETA' plants grown outdoors in Geves, France. The plants were 2 years old. Measurements and numerical values represent averages of typical plant types. Botanical classification: *Hydrangea paniculata* 'RENMETA'.

PROPAGATION

Typical method: Softwood cuttings.
Root initiation: 18 days in summer.
Time to produce rooted cutting: 60 days in summer.
Roots: Thin, freely branching, fibrous. Beige in color, not accurately measured with R.H.S. chart.

PLANT

Growth habit: Semi-upright.
Shape: V-shaped.
Height: Short, about 70 to 80 cm.
Plant spread: 90 to 100 cm.
Pot size of plant described: Plants are in the ground.
Age of plant described: Approximately 2 years.
Stem:
- *Branching*.—Basal.
- *Fasciation*.—Absent.
- *Number of branches*.—About 20 to 28.
- *Shape*.—Rounded, smooth (non-exfoliating).
- *Color*.—Immature: RHS Yellow-Green 146C. Mature: RHS Greyed-Red 181A.
- *Length*.—40 to 500 cm.
- *Width*.—5 to 9 mm.
- *Aspect*.—Straight.
- *Strength*.—Strong and rigid; capable of supporting dense flower heads without falling.
- *Texture*.—Moderate density of lenticels. 10 to 20 per linear cm of stem. Lenticels colored near Yellow-White 158D.

FOLIAGE

Leaf:
- *Arrangement*.—Opposite.
- *Shape*.—Elliptic. No lobing.
- *Length*.—5 to 7 cm.
- *Width*.—4 cm.
- *Apex*.—Acute.
- *Base*.—Obtuse.
- *Margin*.—Shallow serrate.
- *Texture of top surface*.—Coriaceous with little or no rugosity.
- *Texture of bottom surface*.—Coriaceous with little or no rugosity.
- *Pubescence*.—Very slight on upper surface of young leaves.
- *Color*.—Young Foliage, Upper Side: RHS Yellow-Green 144B. Young Foliage, Under Side: RHS Yellow-Green 144C. Mature Foliage, Upper Side: RHS Green 137B. Mature Foliage, Under Side: RHS Yellow-Green 144A.

Venation:
- *Type*.—Pinnate.
- *Color*.—Mature, Upper Side: RHS Yellow-Green 144B. Mature, Under Side: RHS Yellow-Green 144B.

Petiole:
- *Length*.—1 cm.
- *Width*.—2 mm.
- *Color*.—Upper Side: RHS Greyed-Red 181A. Under Side: RHS Greyed-Red 181A.

INFLORESCENCE

Natural flowering season: June to September in France.
Inflorescence type: Mophead.
Panicle:
- *Shape*.—Conical or loose globose.
- *Height*.—8 to 12 cm.
- *Diameter*.—7 to 11 cm.
- *Longevity*.—Approximately 16 weeks.
- *Conspicuousness of fertile flowers*.—Absent or weak.

Fragrance: None.
Sterile flowers:
- *Flowers per inflorescence*.—On average approximately 200.
- *Aspect*.—Outward.
- *Shape*.—Whorl.
- *Length*.—2 cm.
- *Diameter*.—2 cm.
- *Depth*.—3 mm.
- *Persistence*.—Persistent.
- *Longevity*.—Approximately 16 weeks.

Bud:
- *Length*.—5 mm.
- *Diameter*.—5 mm.
- *Shape*.—Obovate.
- *Color*.—RHS Green-White 157A.

Petals:
- *Number*.—4.
- *Arrangement*.—Cruciform.
- *Shape*.—Narrowly elliptic.
- *Tip*.—Acute.
- *Base*.—Blunt.
- *Margin*.—Entire.
- *Length*.—2 mm.
- *Width*.—1 mm.
- *Texture*.—Upper side: Glabrous. Under side: Glabrous.
- *Color*.—Upper Side: RHS White N155A. Under Side: RHS White N155A.

Sepals:
- *Number*.—4 or 5.
- *Arrangement*.—Cruciform or whorl. Moderately overlapping.
- *Shape*.—Elliptic.
- *Tip*.—Rounded.
- *Base*.—Rounded.
- *Margin*.—Entire.
- *Length*.—1 cm.
- *Width*.—6 to 7 mm.
- *Texture*.—Upper side: Glabrous. Under side: Glabrous.
- *Color*.—When Opening, Upper Side: RHS Green-White 157A. When Opening, Under Side: RHS Green-White 157A. Fully Opened, Upper Side: RHS Yellow-Green 145B and 145C mixed with White N155A. Flushed Red-Purple 62A along apex and margins. Fully Opened, Under Side: RHS Yellow-Green 145B and 145C mixed with White N155A. Flushed Red-Purple 62A along apex and margins. Fully mature, upper side: RHS Greyed-Red 182A completely covered with a strong flush of Red-Purple 63A and 63B. Fully mature, under side: RHS Greyed-Red 182A completely covered with a strong flush of Red-Purple 63A and 63B.

Pedicel:
*Length.*—1 cm.
*Diameter.*—1 mm.
*Angle.*—45° to 90°.
*Strength.*—Good, somewhat flexible.
*Texture.*—Pubescent.
*Color.*—RHS Greyed-Red 18AA.

Fertile flowers:
*Flowers per inflorescence.*—About 5 to 10.
*Aspect.*—Upright.
*Conspicuousness.*—Absent or inconspicuous.
*Shape.*—Round, single whorl of petals.
*Length.*—4 mm.
*Diameter.*—4 mm.
*Depth.*—4 mm.
*Persistence.*—Self-cleaning.

Bud:
*Length.*—2 mm.
*Bud diameter.*—2 mm.
*Bud shape.*—Obovate.
*Bud color.*—RHS Green-White 157A.

Petals:
*Number per flower.*—5.
*Arrangement.*—Rotate.
*Shape.*—Elliptic.
*Tip.*—Acute.
*Base.*—Flattened.
*Margin.*—Entire.
*Length.*—2 mm.
*Width.*—1 mm.
*Texture.*—Upper Side: Glabrous. Under Side: Glabrous.
*Color.*—When Opening, Upper Side: RHS Green-White 157A. When Opening, Under Side: RHS Green-White 157A. Fully Opened, Upper Side: RHS Green-White 157D. Fully Opened, Under Side: RHS Green-White 157D.

Sepal:
*Number.*—5.
*Arrangement.*—Rotate.
*Shape.*—Elliptic.
*Tip.*—Acute.
*Base.*—Fused.
*Margin.*—Entire.
*Length.*—1 mm.
*Width.*—1 mm.
*Texture.*—Upper Side: Glabrous. Under Side: Glabrous.
*Color.*—When Opening, Upper Side: RHS Green-White 157A. When Opening, Under Side: RHS Green-White 157A. Fully Opened, Upper Side: RHS Green-White 157D. Fully Opened, Under Side: RHS Green-White 157D.

REPRODUCTIVE ORGANS

Sterile flower:
Stamens:
*Number.*—2 to 8.
*Filament length.*—2 mm.
*Filament color.*—RHS Green-White 157D.
Anther:
*Shape.*—Orbicular.
*Length.*—1 mm.
*Color.*—RHS Green-White 157A.
Pistil:
*Number.*—1.
*Length.*—3 mm.
Stigma:
*Shape.*—3-lobed, fused.
*Color.*—RHS Green-White 157A.
*Style length.*—2.5 mm.
*Style color.*—RHS Green-White 157D.

Fertile flower:
Stamens:
*Number.*—4 to 8.
*Filament length.*—2 mm.
*Filament color.*—RHS Green-White 157D.
Anther:
*Shape.*—Orbicular.
*Length.*—1 mm.
*Color.*—RHS Green-White 157A.
*Pollen amount.*—Sparse.
Pistil:
*Number.*—1.
*Length.*—3 mm.
Stigma:
*Shape.*—3-lobed, fused.
*Color.*—RHS Green-White 157A.
*Style Length.*—2.5 mm.
*Style Color.*—RHS Green-White 157D.

OTHER CHARACTERISTICS

Disease and pest resistance: Neither resistance nor susceptibility to the normal diseases and pests of *Hydrangea* has been observed.

Drought tolerance and cold tolerance: Hardy to USDA Zones 3-8.

What is claimed is:

1. A new and distinct cultivar of *Hydrangea* plant named 'Renmeta' as herein illustrated and described.

* * * * *